United States Patent [19]

Bailey

[11] Plant 4,822

[45] Feb. 9, 1982

[54] ROSE PLANT

[75] Inventor: Dorothy J. S. Bailey, Bakersfield, Calif.

[73] Assignee: San Joaquin Rose Co., McFarland, Calif.

[21] Appl. No.: 185,448

[22] Filed: Sep. 9, 1980

[51] Int. Cl.[3] ..... A01H 5/00

[52] U.S. Cl. ..... Plt./22

[58] Field of Search ..... Plt./22

*Primary Examiner*—James R. Feyrer

*Attorney, Agent, or Firm*—Vincent G. Gioia

[57] ABSTRACT

A new floribunda rose variety of many petaled flowers darkening to signal red upon aging.

1 Drawing Figure

The present invention relates to a new and distinct variety of rose plant of the floribunda rose class, which was originated by my crossing as seed parent the rose known as "Europeana" and the rose known as "Angel Face" as pollen parent.

Among the novel characteristics possessed by this new variety which distinguish it from its parents and all other varieties of which I am aware are large sprays of many petaled blooms beginning as shell pink buds and developing into pink flowers which darken to signal red upon aging. The plant is vigorous but low growing. Asexual reproduction by budding of the new variety as performed in Kern County, Calif., shows that the foregoing and other distinguishing characteristics come true to form and are established and transmitted through succeeding propagations.

The new and improved rose variety which I have developed is an unusually fine floribunda rose capable of producing large sprays of good sized floribunda blooms displayed on a vigorous low growing, free branching plant with abundant foliage.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "37A" is plate 37A of the Royal Horticultural Society Color Chart.

Parentage: Seedling.
*Seed parent.*—"Europeana".
*Pollen parent.*—"Angel Face".
Class: Floribunda.

The following observations are made of specimens grown outdoors in Kern County, Calif., during the months of October and November.

FLOWER

Blooming habit: Continuous.

A. Bud:
(1) *Size.*—Small.
(2) *Form.*—Ovoid.
(3) *Color.*—When speals first divide — 37A to 42D. When petals begin to unfurl — petal edges remain 37A to 42D but predominant bud color becomes 37D.
(4) *Sepals.*—Long, thin, extending beyond bud.
(5) *Peduncle.*—Length — about 1½ inch. Aspect — straight and uniform. Strength — erect. Color — near 146B overlayed with 60B.

B. Bloom:
(1) *Size.*—Average size when fully expanded — about 2½ to 3 inches.
(2) *Borne.*—In large sprays.
(3) *Form.*—Globular, opening ruffled.
(4) *Petalage.*—Number of petals under normal conditions — about 55 to 60.
(5) *Color.*—The color of the bud is 37A to 42D with shell pink 37D showing slightly. As the flower opens the shell pink color becomes more obvious but petal edges retain 37A to 42D coloring. Upon aging the 37A to 42D coloring darkens to signal red 43A. However, individual petals have very pale pink color at point of attachment which extends significantly into the body of each petal. This color contrast is most visible in some of the older blooms where the signal red appears. Occasional petal blackening may also be seen.

C. Petals:
(1) *Texture.*—Thick to medium.
(2) *Appearance.*—Velvety top surface, dull under surface.
(3) *Form.*—Rounded.
(4) *Arrangement.*—Imbricated.
(5) *Petaloids in center.*—Few.
(6) *Persistence.*—Drop off cleanly.
(7) *Fragrance.*—Slight.
(8) *Lasting quality.*—Last well on plant.

REPRODUCTIVE ORGANS

A. Stamens, filaments and anthers:
(1) *Arrangement.*—Regularly arranged around styles.
(2) *Color.*—34C.

B. Pollen:
*Color.*—25C.

C. Styles: Uneven, medium length.

D. Stigmas:
*Color.*—26B.

E. Hips:
*Shape.*—Globular.
*Size.*—Small.

*Color.*—28B.
*Do seeds protude?*—Slightly.

PLANT

A. Form: Compact.
B. Growth: Vigorous, low growing.
*Height attained.*—About 2 to 2½ feet.
C. Foliage: Compound 5 to 7 leaflets.
(1) *Size.*—Small.
(2) *Quantity.*—Abundant.
(3) *Color.*—New foliage: Upper side — bronze green. Under side — near to 147B. Old foliage: Upper side — near 146A. Under side — near 147C.
(4) *Shape.*—Oval.
(5) *Texture.*—Upper side is leathery and under side is dull.
(6) *Edge.*—Serrated.
(7) *Serration.*—Simple.
(8) *Leaf stem.*—Color — near to 146C. Under side — near 146D.
(9) *Stipules.*—Long, smooth.

(10) *Resistance to disease.*—Blackspot — very good. Mildew — good.
D. Wood:
(1) *New wood.*—Color — near 146B with red cast. Bark — smooth.
(2) *Old wood.*—Color — near 146A. Bark — smooth. E. Thorns:
(1) *Thorns.*—Quantity (main stalk) — ordinary. On laterals from stalk — few. Form — flat. Length — small. Color — 146C with red cast. Position — scattered.
(2) Prickles.—Normal.
F. Winter hardiness: Very winter hardy.

I claim:

1. A new and distinct variety of rose plant of the floribunda class, substantially as shown and described, characterized particularly by many petaled flowers borne in large sprays which begin as shell pink buds and mature to signal red blooms displayed on a vigorous plant with abundant foliage.

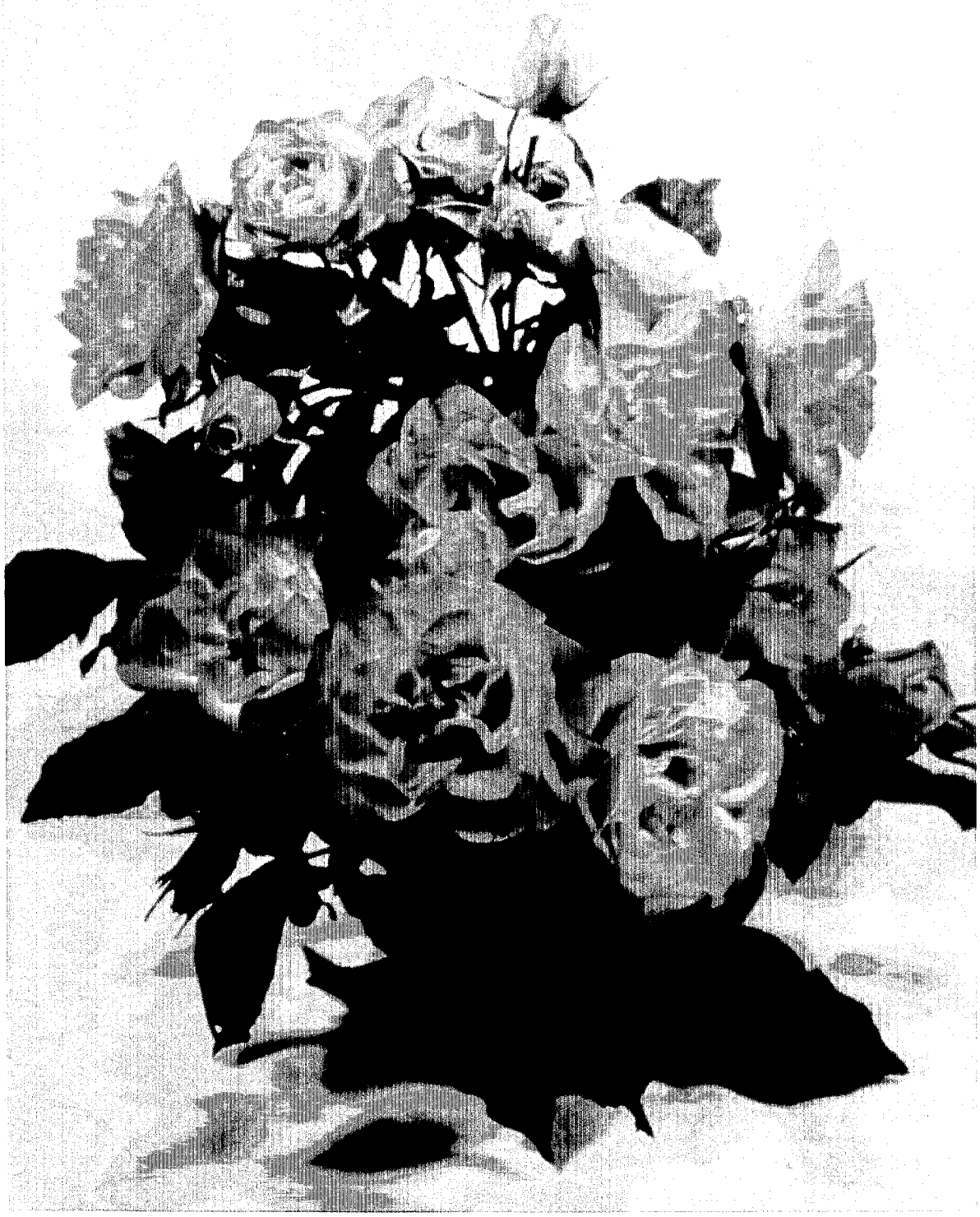

* * * * *